(12) United States Patent
Hampson et al.

(10) Patent No.: US 12,083,120 B2
(45) Date of Patent: Sep. 10, 2024

(54) TREATMENTS

(71) Applicant: DOUGLAS PHARMACEUTICALS LTD, Auckland (NZ)

(72) Inventors: Ian Hampson, Manchester (GB);
Lynne Hampson, Manchester (GB)

(73) Assignee: Douglas Pharmaceuticals LTD., Auckland (NZ)

( * ) Notice: Subject to any disclaimer, the term of this patent is extended or adjusted under 35 U.S.C. 154(b) by 912 days.

(21) Appl. No.: 17/055,067

(22) PCT Filed: May 23, 2019

(86) PCT No.: PCT/IB2019/054293
§ 371 (c)(1),
(2) Date: Nov. 12, 2020

(87) PCT Pub. No.: WO2019/224780
PCT Pub. Date: Nov. 28, 2019

(65) Prior Publication Data
US 2021/0213016 A1 Jul. 15, 2021

(30) Foreign Application Priority Data
May 24, 2018 (GB) .................................. 1808563

(51) Int. Cl.
*A61K 31/513* (2006.01)
*A61K 9/00* (2006.01)
*A61K 9/06* (2006.01)
*A61K 31/427* (2006.01)
*A61K 35/00* (2006.01)
*A61P 35/00* (2006.01)

(52) U.S. Cl.
CPC .......... *A61K 31/513* (2013.01); *A61K 9/0014* (2013.01); *A61K 9/06* (2013.01); *A61K 31/427* (2013.01); *A61P 35/00* (2018.01)

(58) Field of Classification Search
CPC ...... A61P 35/00; A61K 31/513; A61K 9/0014
See application file for complete search history.

(56) References Cited

U.S. PATENT DOCUMENTS

| | | |
|---|---|---|
| 9,782,409 B2 | 10/2017 | Hampson et al. |
| 10,251,884 B2 | 4/2019 | Hampson et al. |
| 11,738,024 B2 | 8/2023 | Hampson et al. |
| 2002/0198160 A1 | 12/2002 | Everitt et al. |
| 2003/0129208 A1 | 7/2003 | Alberts et al. |
| 2005/0143404 A1 | 6/2005 | Rosenberg et al. |
| 2010/0173861 A1 | 7/2010 | Huang et al. |
| 2012/0219602 A1 | 8/2012 | Flack et al. |
| 2016/0271132 A1 | 9/2016 | Hampson et al. |
| 2018/0161328 A1 | 6/2018 | Hampson et al. |
| 2021/0213015 A1 | 6/2021 | Hampson et al. |
| 2022/0257771 A1 | 8/2022 | Hampson et al. |
| 2023/0285287 A1 | 9/2023 | Binnie et al. |

FOREIGN PATENT DOCUMENTS

| | | | |
|---|---|---|---|
| CN | 102083415 A | 1/2011 | |
| EP | 0366277 A2 | 5/1990 | |
| EP | 2613766 A2 | 7/2013 | |
| EP | 3603637 A1 | 2/2020 | |
| WO | 200152821 A1 | 7/2001 | |
| WO | 2004010937 A2 | 2/2004 | |
| WO | 2005007070 A2 | 1/2005 | |
| WO | 2005053694 A1 | 6/2005 | |
| WO | 2011128623 A2 | 10/2011 | |
| WO | 2013034927 A1 | 3/2013 | |
| WO | WO 2013/034927 * | 3/2013 | ............... A61K 9/19 |
| WO | 2015059485 A1 | 4/2015 | |
| WO | WO 2015/059485 * | 4/2015 | ........... A61K 31/427 |
| WO | 2016123541 A1 | 8/2016 | |
| WO | 2019130341 A1 | 7/2019 | |
| WO | 2019224776 A1 | 11/2019 | |
| WO | 2019224777 A1 | 11/2019 | |
| WO | 2019224779 A1 | 11/2019 | |
| WO | 2019224780 A1 | 11/2019 | |
| WO | 2020234800 A1 | 11/2020 | |
| WO | 2021105922 A1 | 6/2021 | |

OTHER PUBLICATIONS

PCT/GB2014/053169 International Search Report and Written Opinion dated Jan. 28, 2015, 11 pages.
PCT/IB2019/054292 International Search Report and Written Opinion dated Sep. 17, 2019, 10 pages.
GB Search Report for GB1808563.9 dated Nov. 23, 2018, 2 pages.
PCT/IB2019/054293 International Search Report and Written Opinion dated Sep. 5, 2019, 8 pages.
Anonymous, Kaletra Cream Attacks HPV, May Stop Cervical Cancer, 2006, retrieved from: http://www.natap.org/2006HIV/082506_02.htm on Jan. 19, 2015, 3 pages.
Batman et al., Lopinavir Up-Regulates Expression of the Antiviral Protein Ribonuclease L in Human Papillomavirus-Positive Cervical Carcinoma Cells, Antiviral Therapy, 2011, vol. 16, pp. 515-525.
Zehbe et al., Lopinavir Shows Greater Specificity than Zinc Finger Ejecting Compounds as a Potential Treatment for Human Papillomavirus-Related Lesions, Antiviral Research, 2011, vol. 91, pp. 161-166.
Mo et al., Characterization of resistant HIV variants generated by in vitro passage with lopinavir/ritonavir, Antiviral Research, 2003, vol. 59(3).
Hampson et al., A Single-Arm, Proof-Of-Concept Trial of Lopimune (Lopinavir/Ritonavir) as a Treatment of HPV-Related Pre-Invasive Cervical Disease, PLOS One, 2016, vol. 11(1).

(Continued)

*Primary Examiner* — Erich A Leeser
(74) *Attorney, Agent, or Firm* — Nixon Peabody LLP

(57) ABSTRACT

The present invention concerns pharmaceutical compositions formulated for dermal application comprising a therapeutically effective amount of lopinavir and ritonavir in a pharmaceutically acceptable vehicle and wherein the weight ratio (w/w) of lopinavir:ritonavir is between 9:1 and 18:1. Such compositions are useful for treating, or preventing, skin cancers and premalignant dermal conditions.

6 Claims, 4 Drawing Sheets

(56) References Cited

OTHER PUBLICATIONS

Glittergalore, 2017, Lopinavir/ritonavir as a topical cream for HPV, CancerCompass, retrieved from: https://www.cancercompass./com/message-board/message/all,133989,0.htm.

International Search Report and Written Opinion for PCT/IB2020/054787 dated Nov. 13, 2020, 19 pages.

Soren Gantt et al., The HIV Protease Inhibitor Nelfinavir Inhibits Kaposi's Sarcoma-Associated Herpesvirus Replication In Vitro, Antimicrobial Agents and Chemotherapy, 2011, vol. 55(6), pp. 2696-2703.

Harmenberg et al., Prevention of ulcerative lesions by episodic treatment of recurrent herpes labialis: A literature review, Acta Derm Venereol, 2010, vol. 90(2), pp. 122-130.

Piret et al., Antiviral resistance in herpes simplex virus and varicella-zoster virus infections: Diagnosis and management, Current Opinion in Infectious Diseases, 2016, vol. 29(6), pp. 654-662.

Katsumata et al., Antiviral efficacy of the helicase-primase inhibitor amenamevir in murine models of severe herpesvirus infection, Biochemical Pharmacology, 2018, vol. 158(1), pp. 201-206.

Kalu et al., Nelfinavir Inhibits Maturation and Export of Herpes Simples Virus 1, Journal of Virology, 2014, vol. 88(10), pp. 5455-5461.

Slyker et al., Acclerated Suppression of Primary Epstein-Barr Virus Infection in HIV-Infected Infants Initating Lopinavir/Ritonavir-Based Versus Nevirapine-Based Combination Antiretoviral Therapy, Clinical Infection Diseases, 2014, vol. 58(9), pp. 1333-1337.

Liu et al., Bowman-Birk inhibitor suppresses herpes simplex virus type 2 infection of human cervical epithelial cells, Viruses, 2018, vol. 10(557), pp. 1-17.

Gantt et al., Nelfinavir Impairs Glycosylation of Herpes Simplex Virus 1 Envelope Proteins and Blocks Virus Maturation, Advances in Virology, 2015, pp. 1-9.

Notice of Allowance for U.S. Appl. No. 17/055,048 dated Dec. 22, 2022, 7 pages.

International Search Report and Written Opinion for PCT/IB2020/061183, dated Mar. 10, 2021, 10 pages.

EPO Exam Report for EP 20760530.4 dated Jan. 18, 2023, 7 pages.

UK Search Report for GB 1917252.7 dated May 22, 2020, 2 pages.

Exam Report for EP 19732473.4 dated Feb. 15, 2023, 3 pages.

\* cited by examiner

TREATMENTS

CROSS-REFERENCE TO RELATED APPLICATIONS

This application is a National Phase of International Application No. PCT/IB2019/054293, filed May 23, 2019, which designated the U.S. and that International Application was published under PCT Article 21(2) in English. This application also includes a claim of priority under 35 U.S.C. § 119(a) and § 365(b) to British patent application No. GB 1808563.9, filed May 24, 2018, the contents of which are herein incorporated by reference in their entirety.

Provided herein are methods and compositions for treating and/or inhibiting the development or progression of skin cancers and benign proliferative disorders of the skin which may or may not be related to infection with viruses. In particular compositions are provided comprising lopinavir and ritonavir for use in treating and/or inhibiting the development or progression of such cancers and disorders

BACKGROUND

Many different forms of cancer exist, and it is believed that there are many different causes of the disease. The incidence of cancer varies, but it represents the second highest cause of mortality, after heart disease, in most developed countries. Current estimates suggest that one in three Americans alive at present will suffer from some form of cancer. There is a well-recognised need to develop new and improved therapies for treating cancers. Furthermore, there is also a requirement to develop therapeutic agents that may be used to inhibit the development of cancer in the general population, susceptible high-risk individuals or as an agent to prevent re-occurrence of disease in individuals already affected.

Globally skin cancers are the most common cancers of all. Melanomas are a significant and aggressive form of skin cancer, but are actually relatively rare compared to non-melanoma skins cancers (NMSCs). NMSCs are principally made up of basal cell carcinomas (BCC) and squamous cell carcinomas (SCC) and the number of cases worldwide exceeds that of all other non-cutaneous cancers combined. In the USA alone there were >5 million cases of NMSC in 2012 (Rogers et al. JAMA Dermatol 2015; 151(10):1081-1086) and, with 4 times this rate, Australia and New Zealand have the highest incidence of this disease in the world. Furthermore, it is also known to be increasing in prevalence (https://www.cancer.org.au/about-cancer/types-of-cancer/skin-cancer.html). In terms of mortality from NMSC, although SCC is usually less common than BCC, it is the most deadly accounting for more deaths whereas BCC is a more indolent disease which does not usually metastasize. There are many factors which contribute to the cause of these malignancies including skin type, exposure to UV radiation, oncogenic viruses, HIV or associated AIDS, immune-suppressive therapy and a variety of chemical carcinogens.

Actinic Keratosis (AK) is a precancerous condition of the skin which has a 20% chance of progressing to SCC if left untreated. Most significantly the prevalence of AK is also higher in susceptible fair-skinned individuals living in areas with high rates of NMSC and who may also be exposed to any of the aforementioned factors which increase the risk of this disease. For example, it has been estimated that 40% of Australians over the age of 40 will develop AK at some time in their lives.

Human tumour viruses are recognised to be a major cause of human cancer and there is a great deal of evidence which supports the contention that these viruses cause cancer by inducing genetic instability in infected cells. For instance, the human papilloma virus (HPV), and particularly types 16 and 18, produce E6 and E7 oncoproteins which are known to induce genetic instability producing abnormal numbers of centrosomes, multinucleation and nuclear atypia. HPV infection is particularly associated with cervical cancer. The inventors noted that cutaneous beta forms of the human papilloma virus (HPV) can synergise with UV and other factors to promote the development of AK (Accardi & Gheit Presse Med. 2014 December; 43 (12 Pt 2): e435-43). In addition, AK can often present as multiple lesions within a defined area which is known as 'field cancerization' and which complicates treatment options.

With regard to current treatments for AK and NMSC, this depends on the extent of disease, the histological type, age of the patient, location of the lesion and whether it is primary or recurrent disease. For example, Mohs surgery is very often used to treat younger people with superficial BCC whereas radiation may be used in older people, particularly if the location of the lesion renders surgery difficult. Although oral systemic treatments have been used to treat NMSC, due to side effects, these are usually restricted for high-risk patients with aggressive recurrent disease. Examples of these are retinoids in conjunction with interferon-α and cisplatin, 5-fluorouracil (5-FU), capecitabine and nonsteroidal anti-inflammatory drugs (NSAIDs) Topically applied treatments have the advantage that they limit systemic exposure to the pharmacological agent and reduce side effects. A variety of these are currently in use such as; 5-FU, Imiquimod, Cidofovir and photodymanic therapy with photo-activated drugs. Surgery is generally considered to be the most effective therapy although the disease often reoccurs which has prompted development of pharmacological alternatives which can be used either as a first line treatment or as an adjunct to surgery (Amaral & Garbe *Expert Opin Pharmacother.* 2017 May; 18(7):689-699).

Conventional topical treatment regimens for AK, SCC and BCC with 5-FU or Imiquimod range from intermittent or continuous application either once or twice daily for periods of between 4 and 16 weeks depending on the type and severity of lesions and the concentration of the drug used. Different treatment regimens of 5-FU and imiquimod together with their efficacy are systematically reviewed in Love et al. 2009 (*Arch Dermatol.* 2009 December; 145(12): 1431-8)

By way of illustration, topical imiquimod cream has 3 strengths; 2.5% (Zyclara); 3.75% (Zyclara) & 5% (Aldara). For AK, imiquimod is indicated for clinically typical, non-hyperkeratotic, non-hypertrophic lesions on the face or scalp in immunocompetent adults using the following doses and regimens: Zyclara 2.5% or 3.75% applied daily to the skin of the affected area for two 2-week treatment cycles separated by 2-week no-treatment period. Aldara 5% can be applied twice a week for 16 weeks to one defined treatment area (contiguous area <25 cm²). For superficial BCC the target tumor should have maximum size of <2 cm diameter and be located on trunk (excluding anogenital skin), neck, or extremities (excluding hands and feet). The treatment area should include 1 cm margins around the tumor with 5% Aldara applied 5 times a week for 6 weeks.

With respect to topical 5-FU treatment for AK, this is available as 0.5% cream (microsphere formulation) which is applied to the affected area once a day. There are also 1%, 2% and 5% creams which are applied twice a day in an amount sufficient to cover the lesions and is continued until the inflammatory response reaches the erosion stage. Duration of therapy is typically 2 to 4 weeks with healing often not occurring for 1 to 2 months following therapy. For BCC, only the 5% cream is used and is applied twice daily in an amount sufficient to cover the lesions. Treatment is continued until the inflammatory response reaches the erosion stage with duration typically 3 to 6 weeks although treatment for extended periods of 10 to 12 weeks may be needed.

A well tolerated, effective, inexpensive, non-surgical, self-applied topical treatment for skin cancers and precancerous dermal conditions would have great potential particularly in view of the expense and toxicity of conventional therapies.

A recent advance in the treatment of cancers caused by viruses is disclosed in WO2015/059485 which describes the protease inhibitors, lopinavir and ritonavir (which had previously been used as orally ingested medicaments for the clinical management of retroviral infections such as HIV) as being clinically useful for topical administration to tissues to prevent or treat malignancies caused by human papilloma virus. The authors were particularly surprised to find that soft capsules of KALETRA® (which were marketed by Abbott/Abbvie for the treatment of HIV infections by oral administration) can be administered topically (e.g. inserted into the vagina for treatment of the cervix) for the prevention or treatment of cervical cancer, for the prevention or treatment of oncogenic viral infections and for the prevention or treatment of benign proliferative orders.

KALETRA® (or its equivalent LOPIMIUNE) is available for oral consumption as a solution comprising 80 mg lopinavir and 20 mg ritonavir per millilitre and was available as a soft capsule for oral administration that comprises 133.3 mg lopinavir and 33.3 mg ritonavir. In both cases the active pharmaceutical ingredients (APIs) are present in a ratio of 4:1 (lopinavir:ritonavir). Given that the authors of WO2015/059485 found soft capsules of KALETRA® to be efficacious, they reasoned that a ratio of 4:1 would be optimal for topical use.

The present invention originates from work carried out by the inventors to formulate a bespoke formulation of lopinavir and ritonavir for topical application to the cervix. They unexpectedly established that the ratio of APIs found in known pharmaceutical products comprising lopinavir and ritonavir (e.g. LOPIMUNE or KALETRA®) are not optimal for treating and/or inhibiting the development or progression of cervical cancers. This work inspired the inventors to try various ratios of lopinavir:ritonavir in models of skin cancer and precancerous dermal conditions. They found that conventional pharmaceutical products comprising lopinavir and ritonavir (e.g. LOPIMUNE or KALETRA®) were also not optimal for addressing pathologies of the skin. The present invention therefore provides compositions comprising optimal ratios of lopinavir:ritonavir for use in treating and/or inhibiting the development or such conditions.

SUMMARY

Disclosed herein are compositions comprising lopinavir in combination with ritonavir for use as a medicament in the treatment of skin cancer or benign proliferative disorders of the skin (e.g. warts) or in the prevention of the development of such cancers and disorders.

According to a first aspect of the invention there is provided a pharmaceutical composition that is formulated for topical application to the dermis comprising a therapeutically effective amount of lopinavir and ritonavir in a pharmaceutically acceptable vehicle wherein the weight (w/w) ratio of lopinavir:ritonavir is between 9:1 and 18:1.

According to a second aspect of the invention there is provided a pharmaceutical composition according to the first aspect of the invention for use as a medicament for treating and/or inhibiting the development or progression of skin cancers and benign proliferative disorders of the skin.

According to a third aspect of the invention there is provided a method of treating and/or inhibiting the development or progression of skin cancers and benign proliferative disorders of the skin in a subject in need of such treatment or inhibition comprising administering a therapeutically effective amount of a pharmaceutical composition according to the first aspect of the invention to said subject.

The compositions are useful for treating a variety of skin cancers (including melanomas). However, in a preferred embodiment the invention concerns treating a subject with, or at risking of developing, a non-melanoma skin cancer. It is most preferred that a subject is treated who has, or is at risk of developing, BCC or SCC.

AK is the main precursor lesion for SCC and as such represents a disorder which may be treated according to the invention.

In one embodiment the cancer or benign proliferative disorder is caused by a viral infection, more preferably by an oncogenic virus and, in particular, human tumour viruses such as human papilloma virus (HPV). The cancer or benign proliferative disorder may be caused by cutaneous beta forms of HPV.

BRIEF DESCRIPTION OF THE DRAWINGS

The summary, as well as the following detailed description, is further understood when read in conjunction with the appended drawings. For the purposes of illustrating the disclosed compositions and methods, there are shown in the drawings exemplary embodiments of the compositions and methods; however, the compositions and methods are not limited to the specific embodiments disclosed. In the drawings.

DETAILED DESCRIPTION

Figure 1:
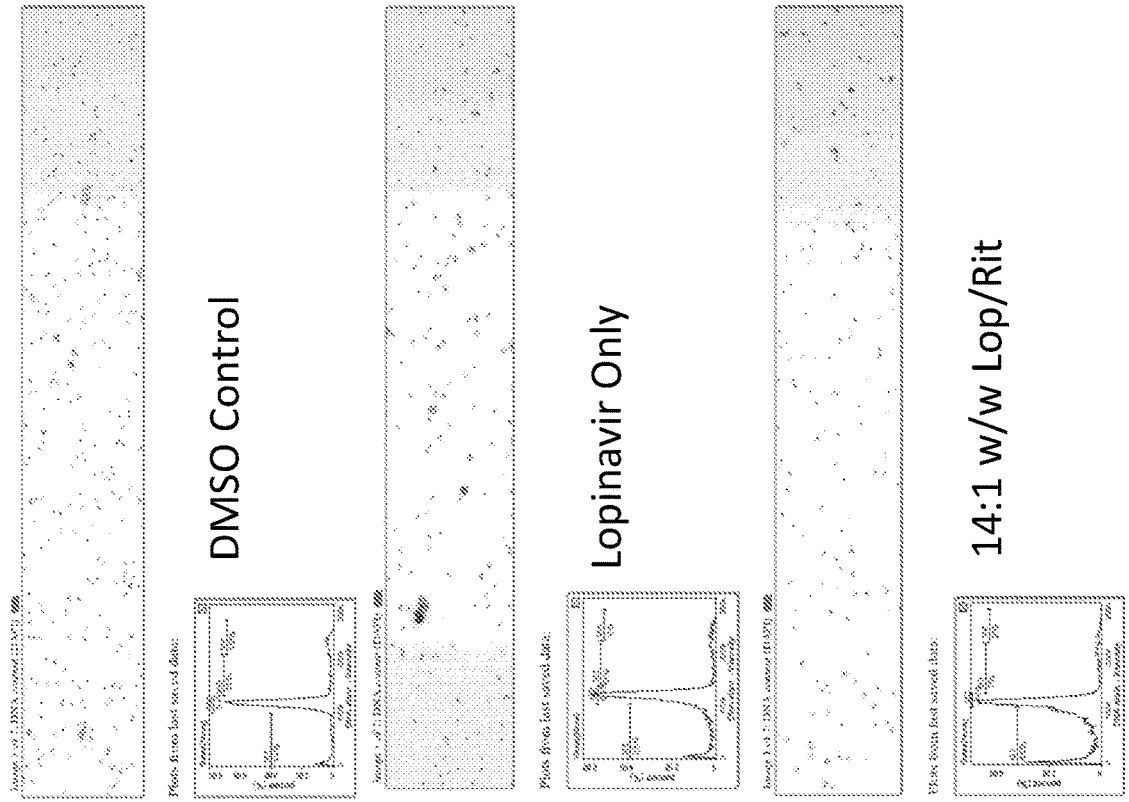
FIG. 1, Shows a typical graphical output of a DNA fragmentation and cell cycle analysis carried out on the NC3000 Image Cell Cytometer (ChemoMetec A/S, Dk) using karyotypically normal, human telomerase immortalised N-Tert human skin keratinocytes treated with DMSO control and different ratios of lopinavir and ritonavir at a total concentration of 20 μM.

The disclosed compositions and methods may be understood more readily by reference to the following detailed description taken in connection with the accompanying figures, which form a part of this disclosure. It is to be understood that the disclosed compositions and methods are not limited to the specific compositions and methods described and/or shown herein, and that the terminology used herein is for the purpose of describing particular embodiments by way of example only and is not intended to be limiting of the claimed compositions and methods.

Reference to a particular numerical value includes at least that particular value, unless the context clearly dictates otherwise. When a range of values is expressed, another embodiment includes from the one particular value and/or to the other particular value. Further reference to values stated in ranges, include each and every value within that range. All ranges are inclusive and combinable.

It is to be appreciated that certain features of the disclosed compositions and methods which are, for clarity, described herein in the context of separate embodiments, may also be provided in combination in a single embodiment. Conversely, various features of the disclosed compositions and methods that are, for brevity, described in the context of a single embodiment, may also be provided separately or in any sub-combination.

The following abbreviations are used herein: human papilloma virus (HPV); non melanoma skins cancers (NMSCs); basal cell carcinoma (BCC); squamous cell carcinoma (SCC); Actinic Keratosis (AK); 5-fluorouracil (5-FU); active pharmaceutical ingredient (API); and nonsteroidal anti-inflammatory drugs (NSAIDs).

As used herein, the singular forms "a," "an," and "the" include the plural.

When values are expressed as approximations, by use of the antecedent "about," it will be understood that the particular value forms another embodiment. Furthermore, the term "about" when used in reference to numerical ranges, cut-offs, or specific values is used to indicate that the recited values may vary by up to as much as 10% from the listed value. As many of the numerical values used herein are experimentally determined, it should be understood by those skilled in the art that such determinations can, and often times will, vary among different experiments. The values used herein should not be considered unduly limiting by virtue of this inherent variation. Thus, the term "about" is used to encompass variations of ±10% or less, variations of ±5% or less, variations of ±1% or less, variations of ±0.5% or less, or variations of ±0.1% or less from the specified value.

As used herein, "treating" and like terms refer to reducing the severity and/or frequency of symptoms, eliminating symptoms and/or the underlying cause of said symptoms, reducing the frequency or likelihood of symptoms and/or their underlying cause, delaying, preventing and/or slowing the progression cancers or benign proliferative disorders, and improving or remediating damage caused, directly or indirectly, by the cancers or disorders.

As used herein, the phrase "therapeutically effective dose" refers to an amount of a composition comprising lopinavir and ritonavir, as described herein, effective to achieve a particular biological or therapeutic result such as, but not limited to, biological or therapeutic results disclosed, described, or exemplified herein. The therapeutically effective dose may vary according to factors such as the disease state, age, sex, and weight of the individual, and the ability of the composition to cause a desired response in a subject. Such results include, but are not limited to, the reduction, remission, and/or regression of the benign or malignant disease or prevention of the development of the benign or malignant disease, as determined by any means suitable in the art.

As used herein, "subject" includes a vertebrate, mammal, domestic animal or preferably a human being.

The "pharmaceutically acceptable vehicle" may be any physiological vehicle known to those of ordinary skill in the art useful in formulating pharmaceutical compositions. The vehicle is most suitably one suited for delivery of the APIs to the skin by topical application.

Disclosed herein are compositions comprising lopinavir and ritonavir for use as a medicament in the treatment of skin cancer or benign proliferative disorders of the skin (e.g. warts) or in the prevention of the development of such cancers and disorders.

Lopinavir (CAS #192725-17-0) is a protease inhibitor chemically designated as [1S-[1R*(R*), 3R*, 4R*]]—N-[4-[(2,6-dimethylphenoxyl)acetyl]amino]-3-hydroxy-5-phenyl-1-(phenylmethyl)pentyl]tetrahydro-alpha-(1-methylethyl)-2-oxo-1(2H)-pyrimidineacetamide. It has the molecular formula $C_{37}H_{48}N_4O_5$ and a molecular weight of 628.80.

Ritonavir (CAS #155214-67-5) is a protease inhibitor chemically designated as 10-Hydroxy-2-methyl-5-(1-methylethl)-1-[2-(1-methylethyl)-4-thiazolyl]-3,6-dioxo-8,11bis(phenylmethyl)-2,4,7,12-tetraazatridecan-13-oic acid, 5-thiazolylmethylester, [5S-(5R*,8R*,10R8,11R*)]. It has the molecular formula $C_{37}H_{48}N_6O_5S_2$ and a molecular weight of 720.95.

Surprisingly, in view of the prior art, the inventors have found that molar ratios of lopinavir:ritonavir for treating, or preventing the development, of skin cancer or benign proliferative disorders of the skin or for prevention of the development of such cancers or such disorders should optimally be in the molar ratio range of 10:1-18:1. In one embodiment the range may be 10.5:1-18:1. Preferably the range is 11.5:1-17:1, more preferably 11.5:1-16.0:1 and even more preferably 11.5:1-15:1 The range may be a molar ratio of about 11.75:1; about 12:1; about 12.5:1; about 13:1; about 13.5:1; about 13.75:1; about 14:0:1; or about 14:5:1.

In another embodiment molar ratio range may be 10:1-16:1. Preferably the range is 10:1-14:1. The molar ratio of lopinavir:ritonavir for treating, or preventing the development, of skin cancer or benign proliferative disorders of the skin or for prevention of the development of such cancers or such disorders may be about 10:1, 12:1 or 14:1.

In a preferred embodiment the molar ratio of lopinavir: ritonavir is about 12:1. In another preferred embodiment the molar ratio of lopinavir:ritonavir is about 13.8:1.

It will be appreciated that lopinavir has a molecular weight of 628.8 daltons and ritonavir has a molecular weight of 720.95 daltons. Accordingly molar ratios and w/w ratios will not be the same and a factor of 0.872 should be applied when converting molar ratios to w/w. Accordingly the inventors have found that w/w ratios of lopinavir:ritonavir for treating, or preventing the development, of cervical cancer or benign proliferative disorders of the cervix or for prevention of the development of such cancers or such disorders may be in the weight ratio range 9:1-18:1. The range may be 10:1-18:1. For instance the range may be 9.5:1-16:1 or 10.0:1-16:1. Preferably the range is 10.0:1-15.0:1, more preferably 10.25:1-14.5:1 and most preferably 10.5:1-13.0:1. The range may be a w/w ratio of about 10.25:1; about 10.5:1; about 10.75:1; about 11:1; about 11.25:1; about 11.5:1; about 11.75:1; about 12.0:1; about 12.25:1; about 12.5:1; about 12.75: about 13.0:1; about 13.25:1; about 13.5:1; about 13.75:1; about 14.0:1 or about 14:25:1. In a preferred embodiment the w/w ratio of lopinavir:ritonavir is about 10.5:1. In a most preferred embodiment the w/w ratio of lopinavir:ritonavir is about 12:1.

The compositions according to the first aspect of the invention are useful in the treatment of skin cancers and particularly useful for treating NMSCs such as BCC and SCC. The invention is applicable particularly, but by no means exclusively, to skin cancers caused by oncogenic viruses, e.g. high-risk or even low-risk forms of human papilloma viruses (HPVs). The compositions are particularly useful for treating cancers associated with infection with cutaneous beta forms of the human papilloma virus (HPV).

The compositions according to the first aspect of the invention are also useful in preventing the development of skin cancers. Accordingly, normal subjects (i.e. subjects with no detectable cancer), subjects with pre-malignant cells or particularly cancer prone subjects may be treated by topical administration of compositions according to the invention with a view to preventing the development of cancer.

Compositions according to the invention are not only useful for treating actual cancers but are also surprisingly useful for treating pre-cancerous conditions, particularly in subjects that may exhibit pre-cancerous AK lesions. Accordingly, compositions comprising lopinavir and ritonavir may be advantageously used to treat such conditions and may also act as a cancer prophylactic.

The invention is applicable particularly, but by no means exclusively, to pre-cancerous conditions and skin cancers caused by oncogenic viruses, e.g. high-risk or even low-risk forms of human papilloma viruses (HPVs). The compositions are particularly useful for treating cancers and disorders associated with infection with cutaneous beta forms of the human papilloma virus (HPV).

The compositions may be given to subjects with a genetic disposition to developing cancer (most particularly BCC or SCC) or even those facing environmental risk (e.g. people exposed to carcinogens, excessive exposure of the skin to the sun etc). In a preferred embodiment, the compositions may be given to people who have had prolonged exposure to the sun and/or subjects with AK.

The compositions may be used to prevent or treat cancer as a monotherapy (i.e. use of the two inhibitors alone) or in combination with other compounds or treatments used in cancer therapy (e.g. chemotherapeutic agents, radiotherapy).

It is most preferred that the compositions are used to treat humans. However, it will be appreciated that the compositions may also have some veterinary use.

Pharmaceutical Compositions

Compositions according to the invention are formulated as a medicament that is suitable for topical application and may in particular be formulated for administration to the skin.

Suitable formulations include, but are not limited to, a gel, cream, paste, ointment or lotion. In some aspects, the pharmaceutical composition can be formulated as a gel. In some aspects, the pharmaceutical composition can be formulated as a cream. In some aspects, the pharmaceutical composition can be formulated as a paste.

In some aspects, the pharmaceutical composition can be formulated as an ointment. In some aspects, the pharmaceutical composition can be formulated as a lotion.

In preferred embodiments, the composition is formulated such that it is suitable for topical delivery of the APIs to the skin (e.g. as an ointment, gel, paste lotion or cream) for preventing the development of, or treating, skin cancers such as BCC or SCC or for preventing the development of, or treating AK.

When used to treat (or prevent the development of) skin cancer, the compositions can be formulated as gels, lotions, paste, creams or ointments that may be applied directly to the skin by techniques known to the art.

Preferred compositions for use according to the invention are formulated for use as skin ointments or creams comprising lopinavir and ritonavir in the weight ratios according to the invention.

In one embodiment, the pharmaceutically acceptable vehicle can be a liquid and the composition can be a solution. In another embodiment, the vehicle can be a gel and the composition can be a gel for applying to the skin. In a further embodiment, the vehicle can be an emulsion (or other pharmaceutically acceptable base) and the composition can be a skin cream. In a further embodiment, the vehicle can be smooth and oily and the composition can be an ointment for application to the skin.

Liquid vehicles may be used in preparing gels, lotions, creams, solutions, suspensions and emulsions. The active ingredient can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, suspending agents, thickening agents, colours, viscosity regulators, stabilizers or osmo-regulators. Suitable examples of liquid vehicles include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). The vehicle can also be an oily ester such as ethyl oleate and isopropyl myristate. The liquid vehicle for pressurized compositions can be halogenated hydrocarbon or other pharmaceutically acceptable propellant.

In one embodiment the composition typically may use polyethylene glycol as a main vehicle for lopinavir and ritonavir. The balance of the vehicle may be made up of, for example, Oleic acid, PEG 35, castor oil, purified water, gelatin, sorbitol special polyol, or any combination thereof. Lopinavir and ritonavir are virtually insoluble in water and it is preferred that such organic bases (or equivalents thereof) are used.

Preferred pharmaceutical compositions are creams, lotions or ointments and comprise vehicles most suited for application to the skin. Some of these formats have water present within the composition. However topical compositions which contain water are not always ideal for use with an API which is prone to degradation by hydrolysis because this may result in a short shelf life of the pharmaceutical product and/or the requirement to store the composition in certain conditions in order to minimize degradation of the active API. Lopinavir and ritonavir are examples of APIs which can be prone to degradation. Therefore, preferred may comprise non-aqueous vehicles. Such vehicles are typically smooth oily compositions and typically contain a significant proportion (w/w) of pharmaceutically acceptable oils or fats (e.g. oleic acid). Such vehicles can contain other suitable pharmaceutical additives such as solubilizers, emulsifiers, buffers, preservatives, suspending agents, thickening agents, colours, viscosity regulators, stabilizers or osmo-regulators.

It will be appreciated that the amount of lopinavir and ritonavir in compositions according to the invention will depend up the exact components and in particular the vehicle for the composition.

By way of example only, suitable amounts of lopinavir in a composition (e.g. the preferred compositions describe below) may be from about 0.1-30% w/w. In some embodiments, the amount of lopinavir in the composition can be from about 1.0-25% w/w. In some embodiments, the amount of lopinavir in the composition can be from 2.0-20% w/w. For instance, and ointment may comprise about 5%, 6%, 10% or 12% (w/w) lopinavir.

Suitable amounts of ritonavir in such compositions may be from about 0.01-3% w/w. In some embodiments, the amount of ritonavir in the composition can be from about 0.1-2.5% w/w. In some embodiments, the amount of ritonavir in the composition can be from 0.15-1.5% w/w. For instance, an ointment may comprise about 0.4775%, 0.5%, 0.625% or 0.955% (w/w) ritonavir.

A preferred composition may comprise about 8 to about 14% by weight of lopinavir and about 0.75 to about 1.4% by weight of ritonavir. For example, the composition may comprise by weight 10% lopinavir and 0.955% ritonavir or the composition may comprise by weight 12% lopinavir and 1% ritonavir.

Another preferred composition may comprise about 4 to about 7% by weight of lopinavir and about 0.375 to about 0.75% by weight of ritonavir. For example, the composition may comprise by weight 5% lopinavir and 0.4775% ritonavir or the composition may comprise by weight 6% weight lopinavir and 0.5% ritonavir.

Compositions for Application to the Skin

A preferred composition for use according to the invention is a pharmaceutical composition comprising:
a. an unsaturated free fatty acid;
b. a stiffening agent; and
c. lopinavir and ritonavir in a weight ratio of between 9:1 and 18:1;
wherein the unsaturated free fatty acid is present at a level of at least 20% by weight of the total pharmaceutical composition weight and wherein the pharmaceutical composition is a semi-solid at room temperature.

The weight ratio of lopinavir:ritonavir may be as defined for the first aspect of the invention. Preferably the weight ratio of lopinavir:ritonavir is between 10:1 and 14:1, more preferably 10:5:1 and 13.5:1 and most preferably about 12.0:1 (w/w).

Conventional compositions employ vegetable oils and/or polysorbates as agents to thicken the composition. It has been advantageously established that an unsaturated free fatty acid and a stiffening agent can be used to prepare a pharmaceutical composition which is a semi-solid at room temperature that can be present in a stationary material state until an external stress is applied resulting in flow of the material. Such an external stress can be the application of the composition to a target tissue (i.e. the skin) and the inventors have found that such compositions are particularly effective for delivering lopinavir and ritonavir to the skin.

Advantageously, the pharmaceutical composition only comprises fats in the form of free fatty acids (unsaturated free fatty acid and/or saturated free fatty acid), for example all fatty acids present in the composition are in the form of a free fatty acid. This allows the pharmaceutical composition to be manufactured at room temperature which is advantageous when the APIs are prone to degradation, and wherein the rate and/or extent of degradation is increased when the API is exposed to heat.

Unsaturated Free Fatty Acids

The unsaturated free fatty acid may be selected from oleic acid, linoleic acid, alpha-linoleic acid, palmitoleic acid, gondoic acid, and ricinoleic acid. The unsaturated free fatty acid is preferably oleic acid.

In one embodiment, of the total unsaturated fatty acid (bound and free form unsaturated fatty acid) present within the composition, at least 90% by weight is in the free form, (i.e. not esterified or bound to other components such as glycerol) At least 95% by weight may be in the free form, at least 98% by weight may be in the free form, at least 99% by weight may be in the free form, or at least 99.5% by weight may be in the free form. The skilled person would be aware of methods used to determine the free fatty acid content versus the total fatty acid content. For example, the free fatty acid content can be measured by reacting the free fatty acid with a chromogenous compound, thus changing the frequency that the chromogeous compound absorbs electromagnetic radiation. Thus, the concentration of the chromogenous compound reacted can be determined by monitoring the chromogenous compound using a suitable wavelength which in turn can be used to determine the free fatty acid content in the sample.

It is to be understood that free fatty acids products that are commercially available may contain small amounts of other free fatty acids. For example, oleic acid typically contains 7-12% saturated free fatty acids, such as stearic and palmitic acid, together with other unsaturated free fatty acids, such as linoleic acid (Handbook of Pharmaceutical Excipients, $2^{nd}$ Edition, see entry for Oleic acid). The terms saturated free fatty acid or unsaturated free fatty acid are to be understood as meaning the saturated free fatty acid or the unsaturated free fatty acid are of Pharmacopeia grade, such as the US Pharmacopeia and/or the British Pharmacopeia, and that the saturated free fatty acid or unsaturated free fatty acid may contain small amounts of other free fatty acids.

In one embodiment, the unsaturated free fatty acid is not in the form of a triglyceride or polysorbate.

The total fatty acid (unsaturated and saturated fatty acids in the bound and free form) present within the composition may be at least 90% by weight, such as at least 95% by weight such as at least 98% by weight, such as at least 99% by weight, or such as at least 99.5% by weight, in the free form, i.e., not esterified or bound to other components such as glycerol.

Stiffening Agents

The stiffening agent is an excipient used to stiffen the composition so that the composition is a semi-solid at room temperature. Conveniently, the stiffening agent is a saturated free fatty acid, such as a $C_{10}$-$C_{38}$ saturated free fatty acid, such as a $C_{16}$-$C_{22}$ free fatty acid. A saturated free fatty acid is a free fatty acid (i.e., the fatty acid is not bound to another molecule, such as glycerol) wherein there are no double bonds between the carbon atoms in the fatty acid. In one embodiment, the stiffening agent is selected from capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid and octatriacontanoic acid. The stiffening agent is preferably stearic acid.

In one embodiment, of the total saturated fatty acid (bound and free form fatty acid) present within the composition, at least 90% by weight, such as at least 95% by weight such as at least 98% by weight, such as at least 99% by weight, or such as at least 99.5% by weight, is in the free form, i.e., not esterified or bound to other components such as glycerol. The skilled person would be aware of methods used to determine the free fatty acid content versus the total fatty acid content. For example, the free fatty acid content can be measured by reacting the free fatty acid with a chromogenous compound, thus changing the frequency that the chromogeous compound absorbs electromagnetic radiation. Thus, the concentration of the chromogenous compound reacted can be determined by monitoring the chromogenous compound using a suitable wavelength which in turn can be used to determine the free fatty acid content in the sample.

In one embodiment, the saturated free fatty acid is not in the form of a triglyceride or polysorbate.

The unsaturated free fatty acid is preferably oleic acid and the stiffening agent is preferably stearic acid.

Other Component of the Compositions

Compositions according to the invention may optionally include a muco-adhesive agent and other excipients as described below.

The compositions may comprise a mucoadhesive agent. The muco-adhesive may be a non-ionic polymer or an ionic polymer. In one embodiment, the non-ionic polymer is a cellulose ether. In one embodiment, the cellulose ether is selected from methyl cellulose, ethylcellulose and hydroxypropylmethylcellulose.

In a preferred embodiment, the muco-adhesive is hydroxypropylmethylcellulose. In one embodiment, the hydroxypropylmethylcellulose has a degree of methoxy substitution of between 19 and 24% by weight and a degree of hydroxypropyl substitution of between 4 and 12% by weight.

In another embodiment, the ionic polymer is sodium polyacrylate.

Optionally, additional excipients may be included in the compositions.

In one embodiment, the composition further comprises a thickener. A thickener is an excipient which when added to a mixture increases the viscosity of the mixture and confers the anhydrous composition with greater physical stability and/or control during delivery of the active pharmaceutical ingredient to the site of application. In one embodiment, the thickener is selected from mono di glyceride, ceresin wax, and hydrogenated vegetable oil.

Preferred Compositions

In one embodiment, there is provided a composition for topical application to the skin comprising:
  a. ritonavir;
  b. lopinavir;
  c. oleic acid; and
  d. stearic acid.

Such a composition may further comprise one, more or all of an ingredient selected from mono di glyceride, ceresin wax, and hydrogenated vegetable oil In one embodiment, there is provided a composition for topical application comprising:
  e. ritonavir;
  f. lopinavir;
  g. hydroxypropylmethylcellulose;
  h. oleic acid;
  i. stearic acid; and
  j. butylated hydroxytoluene In one embodiment, the composition comprises:
  a. about 1.2 to about 1.4% by weight of ritonavir;
  b. about 9 to about 11% by weight of lopinavir;
  c. about 0.5 to 1.5% by weight of hydroxypropylmethylcellulose;
  d. about 55 to about 65% by weight of oleic acid;
  e. about 28 to about 32% by weight of stearic acid; and
  f. about 0.0.5 to about 0.5% by weight of butylated hydroxytoluene;
wherein all % are by weight based upon the total weight of the composition.

In another embodiment, the composition comprises:
  a. about 0.5 to about 0.7% by weight of ritonavir;
  b. about 4 to about 6% by weight of lopinavir;
  c. about 0.5 to 1.5% by weight of hydroxypropylmethylcellulose;
  d. about 55 to about 65% by weight of oleic acid;
  e. about 28 to about 32% by weight of stearic acid; and
  f. about 0.05 to about 0.5% by weight of butylated hydroxytoluene;
wherein all % are by weight based upon the total weight of the composition.

A preferred composition comprises:
  a. ritonavir;
  b. lopinavir;
  c. hydroxypropylmethylcellulose;
  d. oleic acid;
  e. stearic acid;
  f. butylated hydroxytoluene;
  g. mono diglyceride;
  h. ceresin wax;
  i. hydrogenated vegetable oil;
  j. polyoxyl 100 stearate; and
  k. glycerol monooleate;

In one embodiment, the composition comprises:
  a. about 0.9 to about 1.1% by weight of ritonavir;
  b. about 9 to about 11% by weight of lopinavir;
  c. about 0.5 to about 1.5% by weight of hydroxypropylmethylcellulose;
  d. about 55 to about 65% by weight of oleic acid;
  e. about 4 to about 5% of stearic acid;
  f. about 0.1 to about 0.3% by weight of butylated hydroxytoluene;
  g. about 4 to about 6% by weight of mono diglyceride;
  h. about 5 to about 7% by weight of ceresin wax;
  i. about 9 to about 11% by weight of hydrogenated vegetable oil;
  j. about 1 to about 3% by weight of polyoxyl 100 stearate; and
  k. about 2 to about 4% by weight of glycerol monooleate;
wherein all % are by weight based upon the total weight of the composition In one embodiment, the composition comprises:
  a. about 0.9 to about 1.1% by weight of ritonavir;
  b. about 11 to about 13% by weight of lopinavir;
  c. about 0.5 to about 1.5% by weight of hydroxypropylmethylcellulose;
  d. about 50 to about 60% by weight of oleic acid;
  e. about 4 to about 5% of stearic acid;
  f. about 0.1 to about 0.3% by weight of butylated hydroxytoluene;
  g. about 4 to about 6% by weight of mono diglyceride;
  h. about 5 to about 7% by weight of ceresin wax;
  i. about 9 to about 11% by weight of hydrogenated vegetable oil;
  j. about 1 to about 3% by weight of polyoxyl 100 stearate; and
  k. about 2 to about 4% by weight of glycerol monooleate;
wherein all % are by weight based upon the total weight of the composition.

In one embodiment, the composition comprises:
a. about 0.4 to about 0.6% by weight of ritonavir;
b. about 4 to about 6% by weight of lopinavir;
c. about 0.5 to about 1.5% by weight of hydroxypropylmethylcellulose;
d. about 55 to about 65% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition.

In one embodiment, the composition comprises:
a. about 0.4 to about 0.6% by weight of ritonavir;
b. about 5 to about 7% by weight of lopinavir;
c. about 0.5 to about 1.5% by weight of hydroxypropylmethylcellulose;
d. about 55 to about 65% by weight of oleic acid;
e. about 4 to about 5% of stearic acid;
f. about 0.1 to about 0.3% by weight of butylated hydroxytoluene;
g. about 4 to about 6% by weight of mono diglyceride;
h. about 5 to about 7% by weight of ceresin wax;
i. about 9 to about 11% by weight of hydrogenated vegetable oil;
j. about 1 to about 3% by weight of polyoxyl 100 stearate; and
k. about 2 to about 4% by weight of glycerol monooleate;
wherein all % are by weight based upon the total weight of the composition.

Preferred compositions are disclosed in Example 4 and Tables 1-4.

Dosing

It will be appreciated that the amount of lopinavir and ritonavir required is determined by biological activity and bioavailability, which in turn depends, in part, on the precise mode of administration, the physicochemical properties of the composition employed, and whether the compositions are being used as a monotherapy or in a combined therapy with other oral or topical medicines. Indeed, it is also possible that the at least one active pharmaceutical ingredient could be topically applied in addition to oral dosing of the same compounds or other active pharmaceutical ingredient(s). The frequency of administration will also be influenced by the abovementioned factors and particularly the half-life of the active pharmaceutical ingredients within the subject being treated.

Daily doses may be given in the form of a paste, cream, lotion, ointment or similar compositions for topical administration and be applied to the skin once daily, twice daily, thrice daily or as many times per day as a clinician deems necessary.

Preferably the composition is a paste, cream, lotion, ointment or similar composition for topical administration comprising an unsaturated free fatty acid; a stiffening agent (as defined above); and lopinavir and ritonavir in a weight ratio of between 9:1 and 18:1.

In one embodiment, topical treatment regimens for AK, SCC and BCC may range from intermittent or continuous application either once or twice daily for periods of between 4 and 16 weeks depending on the type and severity of lesions and the concentration of the API used.

The treatment area may include 1 cm margins around the lesion (tumor or AK).

AK may be treated with a composition which is applied to the affected area once or twice a day in an amount sufficient to cover the lesions.

Optimal dosages to be administered may be determined by those skilled in the art, and will vary with the strength of the preparation, the mode of administration, and the advancement of the disease condition. Additional factors depending on the particular subject being treated will result in a need to adjust dosages, including, for example, subject age, weight, diet, and time of administration.

Suitable amounts of lopinavir to be given are a daily dose of between about 0.1 mg to about 10.0 g. In some embodiments, the daily dose of lopinavir can be from about 10 mg to about 5.0 g. In some embodiments, the daily dose of lopinavir can be from about 25 mg to about 1.0 g. Conveniently, the daily dose of lopinavir may be between 25 mg and 500 mg (e.g. about 300 mg or 150 mg).

Suitable amounts of ritonavir to be given are a daily dose of about 0.01 mg to about 1.0 g. In some embodiments, the daily dose of ritonavir can be from about 1.0 mg to about 250.0 mg. In some embodiments, the daily dose of ritonavir can be from about 2.5 mg to about 100 mg. Conveniently, the daily dose of ritonavir may be between 5 mg and 50 mg (e.g. about 25 mg, 28.65 mg, 12.5 mg or 14.325 mg).

In one embodiment, about 300 mg of lopinavir and about 28.65 mg of ritonavir per day may be administered to a skin lesion.

In another embodiment, about 150 mg of lopinavir and about 14.325 mg of ritonavir per day may be administered to a skin lesion.

In another embodiment, about 300 mg of lopinavir and about 25 mg of ritonavir per day may be administered to a skin lesion.

In another embodiment, about 150 mg of lopinavir and about 12.5 mg of ritonavir per day may be administered to a skin lesion.

It will be appreciated that the amount of composition which needs to be administered to a subject will depend upon the concentration of lopinavir and ritonavir in the composition and also the size of the lesion which needs to be treated. By way of example preferred compositions (e.g. preferred pastes, creams, lotions or ointments as discussed above) may be administered such that between 0.05 g and 5.0 g of a composition is applied to a 5×5 cm lesion site. More preferably between 0.1 and 4.0 g may be applied to a 5×5 cm lesion site. In one embodiment a 0.5 g (peas sized) amount of a composition may be applied to a 5×5 cm lesion site.

Compositions according to the invention may be rubbed into the skin and left exposed to the air. Alternatively, the compositions may be applied and covered by a dressing (as known to the art) to keep the composition in place and occlude the composition from the air and/or contaminating clothing.

The medicament may be administered to a subject for as long as treatment is required. The length of time for which treatment will be required will depend upon the exact condition being treated or prevented and its severity. A skilled person will appreciate that treatment should be maintained in view of a number of factors which will include any requirement to eradicate any oncogenic virus (e.g.

HPV); to reduce or eradicate cells with a precancerous or cancerous phenotype; or to shrink or eradicate any tumour or other lesion (e.g a wart).

In a preferably embodiment a sufficient amount of a composition may be administered to a subject to provide about 300 mg of lopinavir and about 28.65 mg of ritonavir per day; or about 150 mg of lopinavir and about 14.325 mg of ritonavir per day.

In another embodiment, a sufficient amount of a composition may be administered to a subject to provide about 300 mg of lopinavir and about 25 mg of ritonavir per day; or about 150 mg of lopinavir and about 12.5 mg of ritonavir per day.

In preferred embodiments an ointment disclosed in Table 1,2, 3 or 4 may be topically applied to the skin once or twice per day. Between 0.05 g and 5.0 g of the ointment may be applied to a 5×5 cm lesion site. More preferably between 0.1 and 4.0 g may be applied to a 5×5 cm lesion site. In one embodiment about 3.0 g of the composition may be applied to a 5×5 cm lesion site. In one embodiment about 2.5 g of the composition may be applied to a 5×5 cm lesion site. In one embodiment about 1.0 g of the composition may be applied to a 5×5 cm lesion site. In one embodiment a 0.5 g (peas sized) amount of a composition may be applied to a 5×5 cm lesion site.

EXAMPLES

Example 1: Assessment of the Effects of 8:1-16:1 w/w Ratios of Lopinavir:Ritonavir at a Total API Concentration of 20 µM on hTERT Cells N-TERT cells are an immortalised, non-transformed cell line derived from differentiated cells which are wild type for p53 and karyotypically normal. They proliferate indefinitely and can be transformed by various treatments. These cells therefore represent a good model for evaluating the effect of lopinavir and ritonavir on AK which is a non-transformed and abnormally proliferating precancerous lesion. N-TERT cells, derived from neonatal foreskin keratinocytes, were used in these experiments as described in Dickson et al. (2000) (Mol Cell Biol February 2000 p 1436-1447).

1.1 Methods 1.1.1 Cell Culture

N-TERT cells were cultured by standard methods in Keratinocyte Serum Free Medium (KSFM) supplemented with bovine pituitary extract (BPE) and epidermal growth factor (EGF) at 5% $CO_2$ and 37° C.

Experiments were conducted on cells seeded from a T75 confluent starter culture to T25 flasks which were maintained at 5% $CO_2$ and 37° C. for 5 days. The first 3 days followed standard culture conditions whereas for the following 2 days cells were grown in KSFM plus BPE but minus EGF. This step synchronised cells in their growth cycle and the inventors found this step improved the performance and sensitivity of subsequent assays.

1.1.2 Treatments

After the fifth day, EGF was added back to the cultures along with DMSO control or 20 µM total API's consisting of either Lopinavir alone or different ratios of lopinavir and ritonavir whereupon the incubation was continued for a further 2 days as shown in the results section.

1.1.3 DNA Fragmentation Assays in a NC3000 Image Cytometer (Chemometec Ltd, Norway).

After the final day of culture with the APIs, the cells were trypsinised, pelleted and washed with PBS using standardised procedures. The cells were then fixed in 70% ethanol for a minimum of 4 hours, washed in PBS, counted and then stained with DAPI according to the manufacturers DNA Fragmentation assay procedure (Chemometec Ltd, Dk). Stained cells were then analysed using eight chamber slides with the NC3000 Image Cell Cytometer.

1.2 Results

Figure 2:
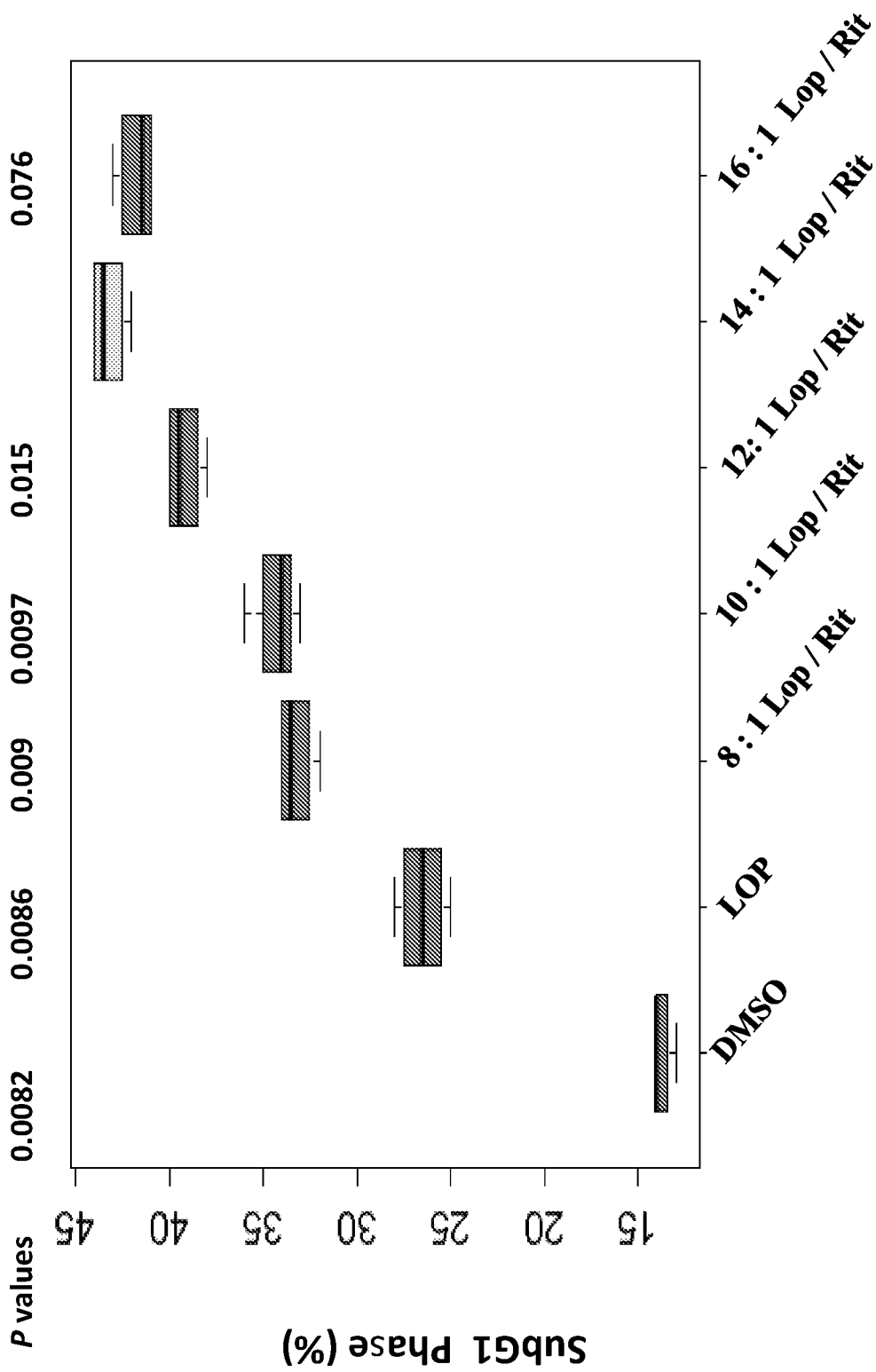
FIG. 2 Shows a box and whisker plot of the complete output of a DNA fragmentation and cell cycle analysis of N-Tert cells treated with different ratios of lopinavir and ritonavir as shown in FIG. 1 where each data point is the product of four separate analyses.

FIG. 1 shows representative images of DAPI stained N-Tert cells that have been treated with DMSO control, lopinavir alone and a ratio according to the invention of 14:1w/w lopinavir:ritonavir. The image cytometer distinguishes cells from 4 phase of the cell cycle depending on quantifying the characteristic DAPI-DNA stain per cell in each sample and a representative output of this is shown in the accompanying graphical analysis. The proportion of cells labelled M1 corresponds to cells undergoing apoptotic DNA fragmentation (Sub G1 where N=<2N DNA) whereas M2-M4 represent normal G1, S and G2 phases of the cell cycle FIG. 2 shows a Box and Whisker plot of DNA fragmentation and cell cycle analysis of N-Tert cells following treatment with lopinavir and ritonavir at 8:1, 10:1, 12:1, 14:1 and 16:1 (w/w) ratios carried out as described in sections 1.1.1-1.1.3 and 1.2. The percentage of apoptotic Sub G1cells with <2N DNA versus those which have intact 2N-4N DNA (G1, S & G2)) was calculated for cells treated with the various treatments and the data presented as Box and Whisker plots which were used in all subsequent figures. The data were also analysed for statistical significance with pairwise permutation test using the R program.

The inventors were surprised to note that a statistically significant peak of apoptotic activity (corresponding to induced cell death of the cells) was apparent for 10:1, 12:1, 14:1 and 16:1 (w/w) of the APIs compared to lopinavir alone or 8:1 (a ratio outside the range of the present invention)(See FIG. 2). FIG. 1 is included to illustrate from where the data of FIG. 2 is derived (see 1.1.3 above).

These data illustrate that lopinavir and ritonavir, in ratios according to the invention, have potential efficacy for treating proliferative disorders of the skin—such as AK.

Example 2: Assessment of the Effects of 10:1-14:1 w/w Ratios of Lopinavir:Ritonavir at a Total API Concentration of 25 µM on HaCaT Cells HaCaT cells are a spontaneously transformed but non-malignant human cell line derived from a skin biopsy (Boukamp et al, (1988) J cell Biol 106(3) p 761-71). The cells exhibit aneuploidy, express a p53 mutation and have a phenotype which is comparable to AK advancing towards a cancerous lesion such as BCC or SCC. This cell line therefore represents a good model for evaluating the effect of lopinavir and ritonavir on precancerous and early stage cancerous conditions of the skin such as AK as evidenced by the reported expression of the anti-apoptotic protein survivin in NMSC, AK and HaCaT cells (Grossman et al. (1999) Lab Invest 79(9) p 1121-6).

2.1 Methods

The basic methods described in 1.1 were followed except:

2.1.1 Cell Culture

HaCaT cells were cultured by standard methods using Dulbecco's Modified Eagle's Medium (DMEM) containing 5% foetal bovine serum (FBS) incubated at 5% $CO_2$ and 37° C. As with N-Tert cells. HaCaT cells were seeded from T75 starter cultures into T25 flasks and expanded for 3 days in DMEM plus 5% FBS. The FBS was then withdrawn and the cells maintained in medium only for a further 3 days at 5% $CO_2$ and 37° C. in order synchronise the growth cycle of the cells.

2.1.2: Treatments

DMEM growth medium containing 5% FCS and either DMSO control or a total API concentration of 25 µM lopinavir only or different ratios of lopinavir and ritonavir were then added to the synchronised HaCaT cells which were maintained at 5% $CO_2$ and 37° C. for a further 3 days. These were then harvested and stained with DAPI for DNA fragmentation cell cycle analysis as described in section 1.1.3

2.2 Results

Figure 3:
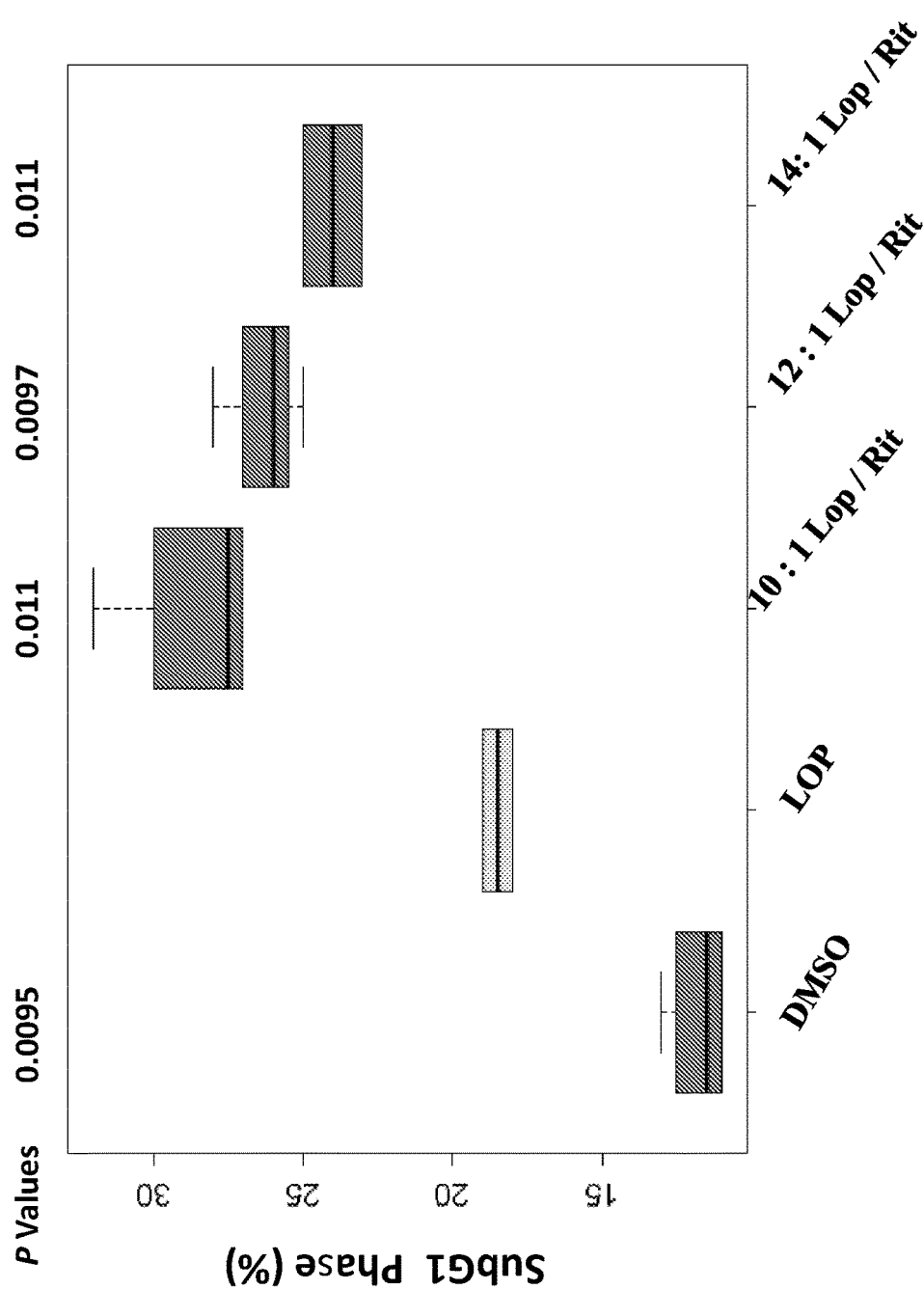
FIG. 3 Shows a box and whisker plot of the complete output of a DNA fragmentation and cell cycle analysis of spontaneously transformed aneuploid human HaCat skin cells treated with different ratios of lopinavir and ritonavir at a total concentration of 25 μM where each data point is the product of four separate analyses.

FIG. 3 shows a Box Whisker plot of the percentage of HaCaT cells which are undergoing apoptotic DNA fragmentation (Sub G1) versus those which have intact 2N-4N DNA (G1, S &G2) following treatment with DMSO (control); 20 µM lopinavir alone; and lopinavir/ritonavir at 10:1, 12:1, and 14:1 (w/w).

The inventors noted that the apoptotic activity caused by lopinavir increased when ritonavir was included at a ratio of 10:1, 12:1 and 14:1.

This illustrates that lopinavir and ritonavir, in ratios according to the invention, will have efficacy for treating proliferative disorders of the skin such as AK by showing activity against cells which are characteristic of AK lesions which are progressing towards skin cancers; and for treating cancers per se.

Example 3: Assessment of the Effects of 8:1, 12:1 and 18:1 w/w Ratios of Lopinavir:Ritonavir at a Total API Concentration of 20 µM on A431 Cells A431 cells are a fully malignant epidermoid carcinoma cell line derived from a skin biopsy taken from an 85 year old woman (https://en.wikipedia.org/wiki/A431_cells). The cells have mutant p53 and are regarded as having a phenotype consistent with NMSC and most particularly SCC (Oleson (2017) Anticancer Drugs 28(10) p 1106-1117). The cell line therefore represents a good model for evaluating the effect of lopinavir and ritonavir on fully malignant NMSC's.

3.1 Methods

The methods described in 2.1 were followed except:

3.1.1: A431 cells were seeded into T25 flasks and expanded for 3 days in DMEM+5% FBS followed by removal of FBS for 2 days to synchronise the cells.

3.1.2: DMEM+5% FCS and either DMSO control or a total API concentration of 25 µM of lopinavir only or lopinavir and ritonavir at the ratios discussed in the results section were then added and the cells incubated for 2 days followed by harvesting for DNA fragmentation and cell cycle analysis as described in section 1.1.3.

3.2 Results

Figure 4:
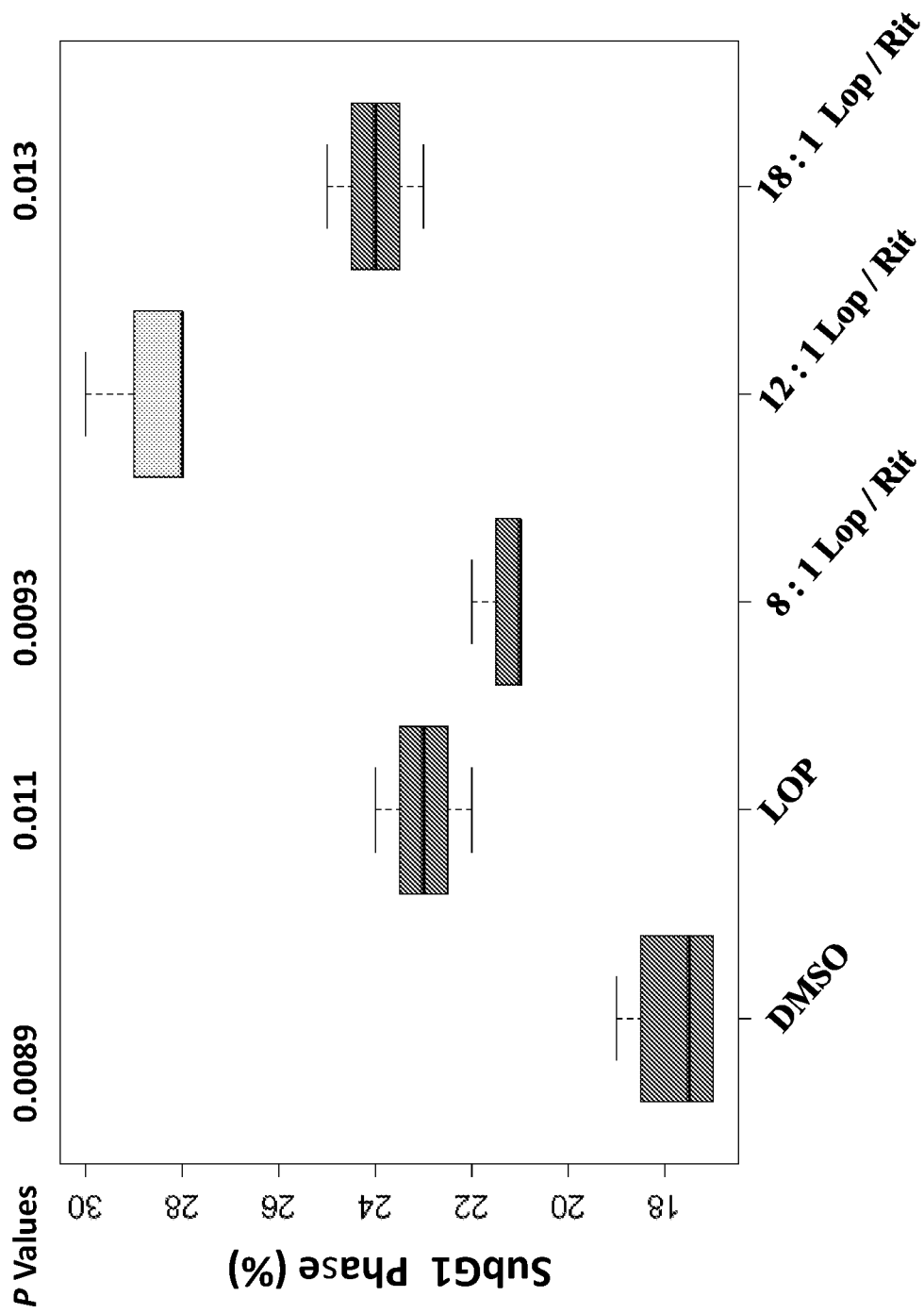
FIG. 4 Shows a box and whisker plot of a DNA fragmentation and cell cycle analysis of the aneuploid A431 SCC cell line treated with different ratios of lopinavir and ritonavir at a total concentration of 25 μM where each data point is the product of four separate analyses.

FIG. 4 shows a Box and Whisker plot of the percentage of A431 cells which are undergoing apoptotic DNA fragmentation (Sub G1) versus those which have intact 2N-4N DNA (G1, S &G2) following treatment with DMSO (control); 20 µM lopinavir alone; and lopinavir:ritonavir at 8:1, 12:1, and 18:1 (w/w).

The inventors noted that the apoptotic activity caused by lopinavir or lopinavir:ritonavir at 8:1 increased when the APIs were included at ratio of 12:1 or 18:1. The improved killing of transformed cells at 12:1 was shown to be highly significant.

This illustrates that lopinavir and ritonavir, in ratios according to the invention, will have efficacy for preventing or treating fully malignant skin cancers such as SCC These data presented in Examples 1-3 illustrate that lopinavir and ritonavir in ratios according to the invention have significantly greater effects on induced cell death than lopinavir alone or lopinavir and ritonavir in ratios that fall outside the range defined for the present invention. The fact that the preferred API ratios were efficacious in each of the cell line models clearly demonstrate the usefulness of lopinavir and ritonavir, in the defined ratios, for treating and/or inhibiting the development or progression of benign proliferative disorders of the skin (e.g. AK); for preventing the progression of proliferative disorders to skin cancer; and for treating malignant skin cancers per se (e.g. BCC or SCC).

Example 4: Preparation of Preferred Formulations

For all formulations present below, all materials used are pharmaceutical grade (either US Pharmacopeia or European Pharmacopeia) except for white ceresin wax, which is Japanese Pharmaceutical Excipient grade.

The manufacture of a composition according to the invention is described below in accordance with Tables 1-4.

i. Add into the mixer the following materials—3,4,5,6,7,8,9,1,10,11 ii. Exclude air from the interior of the vessel iii. Heat to 70° C. while low shear mixing, to achieve a clear, transparent melt.

iv. Add into the mixer the following material—2 v. Exclude air from the interior of the vessel vi. Mix via low shear, to finely disperse the HPMC within the melt vii. Reduce the content temperature to 45° C. while low shear mixing viii. Discharge to storage vessel and exclude air during storage.

ix. Pack composition into aluminium tubes, suitable for dispensing 1.0-5.0 g of composition.

Aluminium tubes may contain a volume of 20-50 mls of composition.

TABLE 1

| # | Ingredient | Function(s) | % w/w |
|---|---|---|---|
| 1 | Oleic acid | Unsaturated free fatty acid | 62.823 |
| 2 | Hypromellose 2208 (4000cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleater | Blending agent | 3.00 |
| 9 | Butylatedhydroxytoluene | Antioxidant | 0.20 |
| 10 | Lopinavir | API | 5.000 |
| 11 | Ritonavir | API | 0.4775 |
| | | TOTAL | 100.000 |

TABLE 2

| # | Ingredient | Function(s) | % w/w |
|---|---|---|---|
| 1 | Oleic acid | Unsaturated free fatty acid | 57.345 |
| 2 | Hypromellose 2208 (4000cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleater | Blending agent | 3.00 |
| 9 | Butylatedhydroxytoluene | Antioxidant | 0.20 |
| 10 | Lopinavir | API | 10.000 |
| 11 | Ritonavir | API | 0.9550 |
| | | TOTAL | 100.000 |

TABLE 3

| # | Ingredient | Function(s) | % w/w |
|---|---|---|---|
| 1 | Oleic acid | Unsaturated free fatty acid | 61.800 |
| 2 | Hypromellose 2208 (4000cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleater | Blending agent | 3.00 |
| 9 | Butylatedhydroxytoluene | Antioxidant | 0.20 |
| 10 | Lopinavir | API | 6.000 |
| 11 | Ritonavir | API | 0.500 |
| | | TOTAL | 100.000 |

TABLE 4

| # | Ingredient | Function(s) | % w/w |
|---|---|---|---|
| 1 | Oleic acid | Unsaturated free fatty acid | 55.300 |
| 2 | Hypromellose 2208 (4000cps) | Muco-adhesive | 1.00 |
| 3 | Mono di glycerides (type 1) | Thickener | 5.00 |
| 4 | White ceresin wax | Thickener | 6.00 |
| 5 | Hydrogenated vegetable oil (type 1) | Thickener | 10.00 |
| 6 | Polyoxyl 100 stearate | Blending agent | 2.00 |
| 7 | Stearic acid | Stiffening agent | 4.50 |
| 8 | Glycerol monooleater | Blending agent | 3.00 |
| 9 | Butylatedhydroxytoluene | Antioxidant | 0.20 |
| 10 | Lopinavir | API | 12.000 |
| 11 | Ritonavir | API | 1.000 |
| | | TOTAL | 100.000 |

Example 5: A Clinical Investigation of the Effects of Topical Treatment with Lopinavir/Ritonavir on Subjects Presenting with Superficial Basal Cell Carcinoma (BCC)

The objectives of the study was to obtain proof-of-concept pilot data on the efficacy of topically applying the ointment of Table 4 as a treatment for superficial BCC; and to assess the tolerability of 3 doses of 0.85 gm per day when topically applied to BCC lesions for a 30 day cycle.

The ointment was packaged in 75 gm tubes with a latex seal and it is intended that a total daily dose of 2.5 gm will be administered with 3 applications of ~0.8 gm which will be well massaged into the lesion.

Example 5 describes a preferred method of administering a preferred composition according to the invention.

The invention claimed is:

1. A pharmaceutical composition that is formulated for dermal application comprising a therapeutically effective amount of lopinavir and ritonavir in a pharmaceutically acceptable vehicle and wherein the weight ratio (w/w) of lopinavir: ritonavir is between 10.25:1 and 14.5:1.

2. The composition according to claim 1 wherein lopinavir and ritonavir are included in a weight ratio of between 10.5:1 and 13:1.

3. The composition according to claim 2 wherein lopinavir and ritonavir are included in a weight ratio of about 12:1.

4. The composition according to claim 1 wherein the composition is formulated as an ointment, gel, paste, cream or lotion.

5. The composition according to claim 1 wherein the pharmaceutically acceptable vehicle is an ointment.

6. The composition according to claim 4 wherein the composition comprises:
 (a) an unsaturated free fatty acid;
 (b) a stiffening agent; and
 (c) lopinavir and ritonavir in a weight ratio of between 10.5:1 and 13.5:1;
 wherein the unsaturated free fatty acid is present at a level of at least 20% by weight of the total pharmaceutical composition weight and wherein the pharmaceutical composition is a semi-solid at room temperature.

* * * * *